(12) United States Patent
Beardsley et al.

(10) Patent No.: US 7,196,060 B2
(45) Date of Patent: Mar. 27, 2007

(54) METHOD TO ENHANCE HEMATOPOIESIS

(75) Inventors: Terry Raymond Beardsley, Escondido, CA (US); Anthony E. Maida, III, Danville, CA (US)

(73) Assignee: S-Cell Biosciences, Inc., Murrieta, CA (US)

(*) Notice: Subject to any disclaimer, the term of this patent is extended or adjusted under 35 U.S.C. 154(b) by 0 days.

(21) Appl. No.: 10/938,451

(22) Filed: Sep. 10, 2004

(65) Prior Publication Data

US 2005/0107300 A1    May 19, 2005

Related U.S. Application Data

(60) Provisional application No. 60/501,959, filed on Sep. 10, 2003.

(51) Int. Cl.
*A61K 38/16* (2006.01)

(52) U.S. Cl. .................... 514/8; 514/21; 530/395; 530/397; 530/399

(58) Field of Classification Search .............. 435/7.1; 514/8, 21; 530/395–399
See application file for complete search history.

(56) References Cited

U.S. PATENT DOCUMENTS 5,032,396 A * 7/1991 Williams .................. 424/85.2
5,616,554 A   4/1997 Beardsley ..................... 514/8

OTHER PUBLICATIONS

Ganser, A., et al. 1990. Effects of Recombinant Human Interleukin-3 in Patients with Normal Hematopoiesis and in Patients With Bone Marrow Failure. Blood. 76(4): 666-676.*
Cairo, M.S., et al. 1991 Pediatric Research 30(6): 554-559.*
Storek, J., et al. May 15, 2003 Blood 101(10): 4209-4218.*
Tiberghien, P., et al. Apr. 1, 1993 Blood 18(7): 1933-1939.*
Goldblum, S.E., et al. 1987 J Applied Physiol 62(1): 122-128.*
Ogawa, Y., et al. 1996 Amer J Hematology 52: 71-76.*
Quill, H., et al. Oct. 1, 1989 Journal of Immunology 143: 2242-2247.*
Buescher, E.S., et al. 1993 Cancer Immunol Immunother 37: 26-30.*
Banda et al., Biol. Blood and Marrow Transplantation (1999) 5(3):162-172.
Beardsley et al., Proc. Nat'l. Acad. Sci USA (1983) 80:6005-6009.
Fuchs et al., AIDS (1991) 5(2):209-212.
Mackall, Stem Cells (2000) 18:10-18.
Nielsen et al., Scand. J. Immunol. (2000) 52:298-303.
Pedersen et al., Science (1987) 235:790-793.
Ulich et al., Blood (1995) 86:971-976.
Ganser et al., Blood (1990) 76(4):666-676.
International Search Report for PCT/US04/29400, mailed on Feb. 22, 2005, 3 pages.
Sonoda et al., Proc. Natl. Acad. Sci. USA (1988) 85:4360-4364.

\* cited by examiner

*Primary Examiner*—Robert A. Wax
*Assistant Examiner*—Marsha Tsay
(74) *Attorney, Agent, or Firm*—Morrison & Foerster LLP

(57) ABSTRACT

The present invention relates generally to the fields of immunology and molecular biology, and particularly to a method for treating hematopoietic disorders. The invention provides a method to treat a deficiency of one or more types of blood cells in a mammal, which includes administering an effective amount of TISF or of a compound that stimulates CD4+ cells like TISF does. In one embodiment, TISF that originates from a mammalian species is administered to a mammalian subject diagnosed as having a deficiency in one or more types of blood cells.

7 Claims, 3 Drawing Sheets

**The study included 23 cats with FIV/Feline Leukemia. There is currently NO treatment that works for these cats.

**The study included 23 cats with FIV/Feline Leukemia. There is currently NO treatment that mechanism for these cats.

Effect of S-Celergin on Platelet Recovery

METHOD TO ENHANCE HEMATOPOIESIS

CROSS-REFERENCE TO RELATED APPLICATIONS

This application claims priority under 35 U.S.C. § 119(e) to U.S. Provisional Application Ser. No. 60/501,959, filed Sep. 10, 2003; the contents of that application are incorporated herein by reference.

BACKGROUND OF THE INVENTION

Mammalian blood contains a wide variety of different types of cells, including red blood cells (erythrocytes), platelets, and white blood cells (leukocytes). White blood cells (leukocytes), in turn, include several different cell types, notably the lymphocytes, monocytes, and several types of granulocytes such as neutrophils, eosinophils, and basophils. These various types of cells comprise a major part of the complex and critical mammalian immune system. Most of them are short lived and must be replaced every few hours, days, weeks, or months, and all of them are formed by differentiation and proliferation of a single type of pluripotent stem cells which reside in the bone marrow.

The process by which a single kind of stem cell differentiates to form many different mature cells which cannot themselves proliferate is called hematopoiesis. It involves the formation of precursors for each of these different kinds of cells from a single kind of stem cell, which occurs in bone marrow, and proliferation and differentiation into the specialized cell types, which occurs principally in the bone marrow, spleen, thymus, and lymph nodes. The process is controlled by a complex system of signals that attempts to maintain an appropriate balance among all of these different types of cells so that the immune system operates effectively.

Some disease states and infections dramatically affect hematopoiesis, resulting in depletion of certain types of blood cells. For example, HIV infection often causes anemia (red blood cell deficiency), neutropenia (neutrophil deficiency), or thrombocytopenia (platelet deficiency), or various combinations of these states, including pancytopenia, which is a deficiency of all different types of blood cells. See N. K. Banda, et al., Depletion of CD34+CD4+ Cells in Bone Marrow from HIV-1 Infected Individuals, Biol. Blood and Marrow Transplantation, 5(3), 162–172 (1999). See also D. Fuchs, et al., AIDS, 5(2), 209–212 (1991)Similarly, various radiation and chemotherapy regimens may severely compromise the immune system by depleting one or more of these cell types. See C. L. Mackall, Stem Cells 18, 10–18 (2000). Radiation therapy, for example, can destroy most of the highly sensitive and surprisingly rare stem cells, resulting in an inability to rapidly regenerate cellular components of the blood.

Regardless of whether it is caused by an organic disorder, infection, or therapeutic treatment, severe deficiency of any of these cellular components of the blood and the immune system can result in direct physical symptoms (such as anemia where red blood cells are depleted, or bleeding disorders where platelets are depleted) or in greatly increased susceptibility to secondary infections. Thus methods for treating deficiencies of various types of blood cells are needed, as are methods for preventing such deficiencies that would otherwise result from treatment of other disorders such as cancers or viral infections. The present invention provides methods for increasing levels of various types of blood cells in a subject experiencing a deficiency in the level of one or more types of blood cells.

BRIEF SUMMARY OF THE INVENTION

T-4 immune stimulating factor ("TISF") has been shown to provide immune-boosting activity, apparently due to its ability to stimulate IL-2 production over a period of several days at the site where it is needed. See U.S. Pat. No. 5,616,554. The molecule is described in the foregoing patent as a 50K Dalton protein with an isoelectric point of 6.5. In the present disclosure, the same molecular entity has now been demonstrated to contain the ability to promote hematopoiesis possibly by its known mechanism of action to stimulate CD4+ lymphocytes. It is hypothesized that CD4+ lymphocytes may regulate the production of all blood cell types in the bone marrow, including red blood cells, platelets, and granulocytes. A deficiency in CD-4 lymphocytes thus could lead to the pancytopenia observed in immune compromised subjects including cancer patients undergoing chemotherapy, or viral or other chemically induced conditions.

In the prior patent, administering TISF was shown to increase the effectiveness of a distemper vaccine in canines, boost the titer of antibody to influenza virus in mice, and reduce the symptoms of feline immunodeficiency virus (FIV) in infected cats. Thus it exhibits an ability to enhance the effectiveness of a healthy immune system. It has now been shown that TISF also acts to stimulate the production of certain types of blood cells where a deficiency of such cells has developed. Thus TISF is now shown to accelerate the recovery of platelet counts following chemotherapy-induced platelet deficiency in a murine model system.

It is well known that AIDS patients suffer profound CD4+ lymphocyte deficiency, but a less well appreciated observation is that many immune deficient subjects have concomitant anemia, granulocytopenia, and thrombocytopenia. In fact, an emerging paradigm in oncology is that cancer patients suffer a profound and chronic CD4+ lymphocyte deficiency. C. L. Mackall, Stem Cells 18, 10–18 (2000).

In the present disclosure, the observation was made in studies of feline immunodeficiency virus (FIV) and feline leukemia virus (FeLV) infected cats that when lymphocytes were increased by TISF administration (the focus of the study and U.S. Pat. No. 5,616,554), red cells, platelets and granulocytes increased also. See FIGS. 1, 2, 3, and 4. Based upon these preliminary observations, a mouse model of chemotherapy-induced platelet deficiency was used to confirm the effect of TISF on platelet recovery. See T. R. Ulrich, et al., Blood, 86, 971–71 (1995). The data are illustrated in FIG. 5.

The data indicated that administering TISF can accelerate the recovery of platelet counts following chemotherapy-induced deficiency. It is contemplated that doses ranging from 0.1 µg/kg to 500 mg/kg would be effective. The route of administration could be parenterally, intraperitoneally, topically, or orally. A dose regimen of treatment may be once, twice or three times daily, weekly, semi-weekly, or monthly. Clinical application to the treatment of pancytopenias in cancer patients and other viral or chemically-induced immune deficiency conditions is suggested. Further confirmation of theses observations in additional animal models of hematological deficiencies is in progress.

In one aspect, the present invention provides a method to increase the levels of specific types of blood cells in a patient exhibiting a deficiency in one or more types of blood cells. The method includes administering an effective amount of TISF, or a compound that stimulates CD4+ cells like TISF does, to a subject who has been diagnosed as having a deficiency of red blood cells, platelets, or white blood cells.

In one embodiment, the present invention provides a method to stimulate the production of red blood cells (erythrocytes) in a subject diagnosed as having a deficiency of red blood cells; the method includes administering to the subject an amount of TISF (T-4 immune stimulating factor) that is sufficient to elevate the subject's red blood cell count. In one such embodiment, the subject has been diagnosed as suffering from anemia.

In another embodiment, the present invention provides a method to stimulate the production of granulocytes in a subject diagnosed as having a level of granulocytes that is lower than desired; the method includes administering to the subject an amount of TISF (T-4 immune stimulating factor) that is sufficient to elevate the subject's granulocyte count.

In yet another embodiment, the present invention provides a method to stimulate the production of platelets in a subject diagnosed as having a level of platelets that is lower than desired; the method includes administering to the subject an amount of TISF (T-4 immune stimulating factor) that is sufficient to elevate the subject's platelet count.

In another aspect, the present invention provides a method to stimulate production of specific types of blood cells in a subject diagnosed as having a deficiency in levels of one or more types of blood cells. The method includes administering to the subject in need of treatment an effective amount of a compound that stimulates CD4+ cells like TISF does.

In one embodiment, the present invention provides a method to stimulate the production of red blood cells (erythrocytes) in a subject diagnosed as having a deficiency of red blood cells. The method includes administering to the subject an amount of a compound that stimulates CD4+ cells that is sufficient to elevate the subject's red blood cell count. In one such embodiment, the subject has been diagnosed as suffering from anemia. In a preferred embodiment, the compound that stimulates CD4+ cells is selected from the group consisting of IL-1, IL-2, IL-3, IL-4, IL-6, IL-7, IL-12, γ-interferon, TNF-α, anti-CD3 antibody, CD28, and superantigens such as toxic shock syndrome toxin-1 (TSST-1), streptococcal pyrogenic exotoxin (SPE), and staphyloccal enterotoxins.

In another embodiment, the present invention provides a method to stimulate the production of granulocytes in a subject diagnosed as having a level of granulocytes that is lower than desired; the method includes administering to the subject an amount of a compound that stimulates CD4+ cells that is sufficient to elevate the subject's granulocyte count. In a preferred embodiment, the compound that stimulates CD4+ cells is selected from the group consisting of IL-1, IL-2, IL-3, IL-4, IL-6, IL-7, IL-12, γ-interferon, TNF-α, anti-CD3 antibody, CD28, and superantigens such as toxic shock syndrome toxin-1 (TSST-1), streptococcal pyrogenic exotoxin (SPE), and staphyloccal enterotoxins.

In yet another embodiment, the present invention provides a method to stimulate the production of platelets in a subject diagnosed as having a level of platelets that is lower than desired; the method includes administering to the subject an amount of a compound that stimulates CD4+ cells that is sufficient to elevate the subject's platelet count. In a preferred embodiment, the compound that stimulates CD4+ lymphocytes is selected from the group consisting of IL-1, IL-2, IL-3, IL-4, IL-6, IL-7, IL-12, γ-interferon, TNF-α, anti-CD3 antibody, CD28, and superantigens such as toxic shock syndrome toxin-1 (TSST-1), streptococcal pyrogenic exotoxin (SPE), and staphyloccal enterotoxins.

In another aspect, the present invention provides a therapeutic protocol for treatment of a subject experiencing a deficiency in the level of one or more types of blood cells. The protocol includes diagnosing the subject as having a deficiency in the level of a specific type of blood cell, then treating the subject with TISF in an amount effective to increase the level of the type of blood cell in which the subject is deficient.

In one embodiment, the present invention provides a therapeutic protocol that comprises diagnosing a subject as having a less than desirable level of red blood cells, followed by administering to said subject an amount of TISF effective to elevate red blood cell count in that subject. In this embodiment, the subject may be one suffering from anemia.

In another embodiment, the present invention provides a therapeutic protocol that comprises diagnosing a subject as having a less than desirable level of granulocytes, followed by administering to said subject an amount of TISF effective to elevate granulocyte count in that subject.

In yet another embodiment, the present invention provides a therapeutic protocol that comprises diagnosing a subject as having a less than desirable level of platelets, followed by administering to said subject an amount of TISF effective to elevate platelet count in that subject.

The subject for each of the above embodiments is a mammal. In preferred embodiments, the subject may be canine, bovine, or feline. Embodiments wherein the subject is human are more preferred. The TISF used for the present invention may be derived from an animal source or from a cell culture. In preferred embodiments, TISF is produced by a cell culture method such as that described in U.S. Pat. No. 5,616,554, wherein the DNA encoding the TISF originated from a mammalian source. Preferred mammalian sources for TISF are canine, bovine, feline and human, and it is often most preferred to utilize TISF which is produced from DNA which came from the same species as the subject to be treated.

BRIEF DESCRIPTION OF THE DRAWINGS

FIG. 1 shows increased lymphocyte counts; FIG. 2 shows increased red blood cell counts; and FIG. 3 shows increased granulocyte counts. In each case, the Figures show that animals having a specific blood cell deficiency showed substantial improvement after a single dose of TISF, with the greatest increase seen in animals with severe deficiencies.

DETAILED DESCRIPTION OF THE INVENTION

Figure 1:
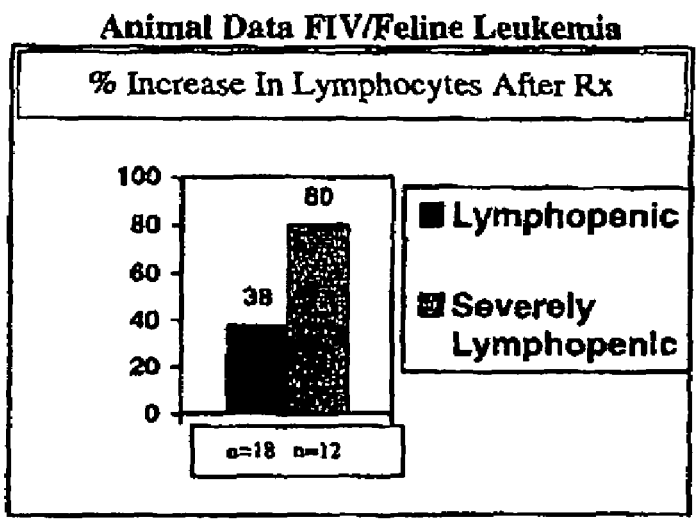
FIGS. 1–3 summarize the results of administering a single dose of TISF to cats infected with either FIV or FeLV.

As used in the present disclosure, "hematopoiesis" refers to the processes by which new blood cells are formed from stem cells and subsequently develop through precursor stages into mature blood cells. It includes the regulation of this process, and the formation of immature precursors of the mature blood cells as well as the differentiation process and the positive and negative selection processes involved.

The term "TISF" refers to a mammalian polypeptide or mixture of polypeptides of mammalian origin; the preparation of TISF and its characterization as a novel entity are described in U.S. Pat. No. 5,616,554, which is herein incorporated by reference in its entirety. TISF is alternatively referred to as Epithyme™ and as S-Celergin at times herein and in other references. A number of factors have been described which stimulate various stages of CD4+ lymphocyte development. TISF stimulates a normally unresponsive population of cells at a later stage of the process while a factor stimulating an earlier stage of the process is described, for example, in Beardsley, et al., PNAS 80: 6005 (1983). TISF is thus effective as described in U.S. Pat. No. 5,616,554 for stimulation of mature T-lymphocytes, resulting in increased antiviral or antitumor activity. Herein, its effectiveness for the treatment of conditions characterized by a deficiency of at least one type of blood cell chosen from the group consisting of red blood cells, platelets, and granulocytes is disclosed. TISF provides relief from these conditions by stimulating the formation of more blood cells of the type needed to alleviate such deficiency.

The term "granulocytes" refers to any member of the class of leukocytes characterized by the presence of many granules in the cytoplasm, and includes neutrophils, eosinophils and basophils.

The term "superantigens" refers to compounds such as toxic shock syndrome toxin-1 (TSST-1), streptococcal pyrogenic exotoxin (SPE), and staphyloccal enterotoxins, which independently stimulate T-4 cells at extremely low concentrations (picomolar to femtomolar) in the absence of antigen, causing the rapid activation of large numbers of T-4 lymphocytes.

TISF may be obtained by purification from a host animal, but is preferably obtained by purification from a cell culture by methods such as those described in U.S. Pat. No. 5,616,554, which is herein incorporated by reference in its entirety. TISF may be of feline, canine, or bovine origin; in a preferred embodiment, the TISF administered to a subject originates from the same species as that of the subject to be treated. TISF may be used to treat hematopoietic disorders in canine, feline, and bovine subjects as well as in human subjects.

TISF, or a compound that stimulates CD4+ cells like TISF does, may be administered parenterally, intraperitoneally, topically or orally. Parenteral administration is often preferred, and intraperitoneal administration is sometimes preferred. The TISF, or the compound that stimulates CD4+ cells like TISF does, may be admixed with pharmaceutically acceptable diluents, excipients, stabilizing agents, solubilizing agents, or other pharmaceutically-indicated agents, and it may optionally be incorporated into a liposomal or slow-release matrix for administration.

Suitable pharmaceutical carriers and diluents, as well as pharmaceutical necessities for their use in pharmaceutical formulations, are described in Remington's Pharmaceutical Sciences (Alfonso Gennaro et al., eds., 17th edn., Mack Publishing Co., Easton Pa., 1985), a standard reference text in this field, in the USP/NF, and by Lachman et al. (The Theory & Practice of Industrial Pharmacy, 2nd ed., Lea & Febiger, Philadelphia Pa., 1976). In the case of rectal and vaginal administration, the compositions are administered using methods and carriers standardly used in administering pharmaceutical materials to these regions. For example, suppositories, creams (e.g., cocoa butter), or jellies, as well as standard vaginal applicators, droppers, syringes, or enemas may be used, as determined to be appropriate by one skilled in the art. Intravenous, intramuscular, intraperitoneal, or other types of injection administration are often advantageous, especially for TISF, since it may be subject to degradation if administered orally or topically; suitable compositions for such administration are well known to those skilled in the art, and may be identified by analogy to other polypeptide pharmaceutical compositions.

The compositions of the invention may be administered by any route clinically indicated, such as by application to the surface of mucosal membranes (including: intranasal, oral, ocular, gastrointestinal, rectal, vaginal, or genito-urinary). Alternatively, parenteral (e.g., intravenous (IV), subcutaneous, intraperitoneal, or intramuscular) modes of administration may also be used. Because TISF is a polypeptide, and is thus subject to degradation upon oral or topical administration, administration by parenteral (injection) methods including intravenous delivery is often preferred. To maximize its efficient utilization, intravenous delivery of TISF is often preferred and such delivery may be concurrent with delivery of other nutrient, hydration or therapeutic agents as appropriate. For intravenous administration, TISF is preferably dissolved in an aqueous or isotonic solution such as saline; phosphate buffer may be added as needed to ensure stability of the composition. Further details of compositions suitable for administration of TISF are well-known to those of skill in the art by analogy to other pharmaceutical compositions which contain polypeptides as active ingredients.

The amount of TISF to be administered depends on the particular subject and indications: where multiple cytopenias or pancytopenia is to be treated, the dosage may be increased accordingly, while a lower dosage may be appropriate for treatment of a deficiency in a single type of blood cell. The mode and frequency of administration can also be determined according to the desired effect, as one skilled in the art will appreciate, and the effectiveness of the chosen regimen can readily be ascertained by monitoring improvements in the levels of the blood cells of interest, allowing the regimen to be optimized for the particular subject being treated. In general, TISF will be administered in compositions which deliver amounts of TISF ranging between about 1 µg and 500 mg per kilogram of body weight of the subject. Preferred doses are generally between about 5 µg/kg and 100 mg/kg, and more preferably between about 10 µg/kg and 50 mg/kg. A dosage of about 10 µg/kg to 10 mg/kg is often more preferred.

Administration may be repeated as is determined to be necessary by one skilled in the art, considering the severity of the subject's blood cell deficiency and what other treatments the subject is receiving, or it may be delivered continuously to a subject via an intravenous fluid delivery system. While a single administration of TISF has been demonstrated to produce effects lasting for several days to several weeks, repeated administration at intervals of a few hours to a month are contemplated and are within the scope of the invention. Thus TISF may be administered one to three times daily, or it may be administered one or two times per week, or one to two times per month. Determination of the dose required and the frequency of treatment required are within the ordinary skill in the art, since dosage and frequency can be adjusted until the desired effect is achieved. Progress is readily monitored by well-known techniques for determining the blood cell count for each type of blood cell of interest for the particular subject.

Since TISF may be used to alleviate the anticipated side effects of antiviral, antitumor, or other therapies, it is also contemplated that TISF may be admixed with or administered with such therapeutic agents, including but not limited to antiretroviral agents such as HIV protease inhibitors and reverse transcriptase inhibitors, radiotherapeutic treatments, and antineoplastic therapeutic agents such as alkylating agents, purine nucleoside analogs, and corticosteroids. Compositions containing a mixture of such other therapeutic agents with TISF are thus contemplated, as are treatment protocols which utilize TISF in combination with such agents.

ADMINISTRATION OF TISF

TISF may be administered to a subject via various means, including parenteral (especially intravenous dlivery), oral, topical and intraperitoneal administration. A minimally effective dosage of TISF was determined to be about 1 µg/kg of the recipient subject's body weight; preferably, at least about 5 µg TISF per kilogram of the subject's body weight is administered to the animal, with an upper limit of about 500 mg/kg. TISF may efficaciously be administered alone or in combination with another immune potentiator, and may be incorporated in a pharmaceutically acceptable carrier or excipient. It may also be incorporated into an isotonic solution for intravenous administration.

For treatment of feline immunodeficiency virus (FIV) or feline leukemia (FeLV) infection, cats may advantageously be injected with 1 ml of the above product. For treatment of canine or human infections, increased doses are used to adjust for their increased mass and body surface area of the particular subject to be treated.

The present invention can be better understood by way of the following examples which are representative of certain preferred embodiments thereof, but which are not to be construed as limiting the scope of the invention.

EXAMPLE I

Cats ranging in age from one to three years were obtained from Dr. Janet Yamamoto at the University of California at Davis. The cats were experimentally infected with the Petaluma strain of FIV as controls in a vaccine trial. (See Pedersen, et al., Science 235: 790–93 (1987), which is incorporated herein by reference.) All cats were determined to be FIV positive by Dr. Yamamoto but manifested no disease symptoms upon arrival at the test facility.

The basic testing protocol is as follows:
1. Allow felines to rest and acclimate for about two weeks.
2. Obtain blood samples prior to initiation of treatment for baseline determination of lymphocyte counts and/or T4/T8 ratios.
3. Randomly assign felines to treatment or control groups.
4. Inject treatment group felines subcutaneously with 1.0 ml feline TISF in purified or semipurified form.
5. Obtain blood samples on a weekly basis prior to each injection. Monitor clinical signs and record findings.
    6. Obtain bone marrow and/or blood sample for use in FIV detection test in treatment and control animals (e.g., appropriate staining of blood smears).

Figure 2:
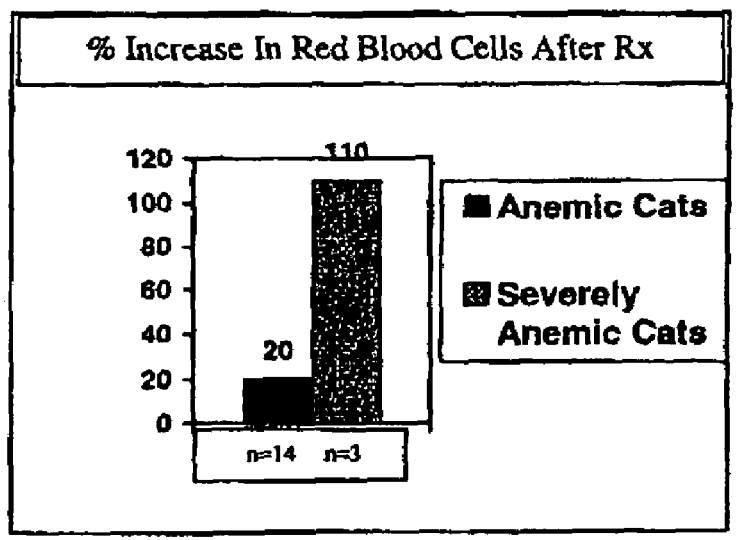
Figure 3:
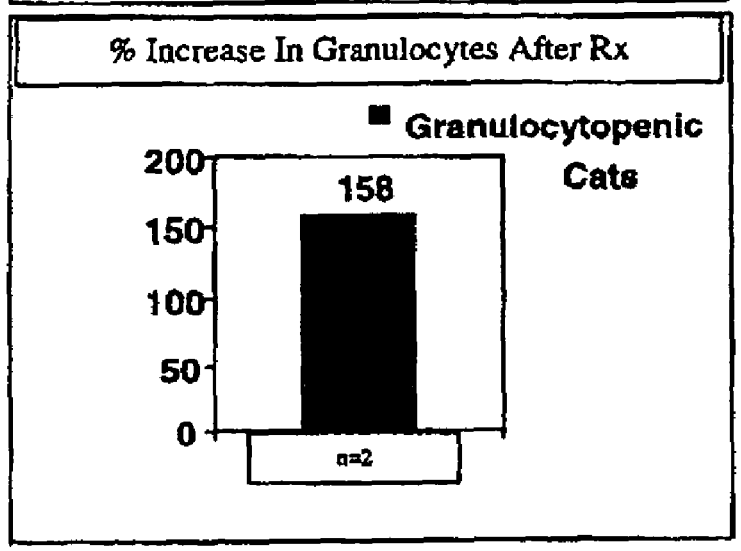
Figure 4:
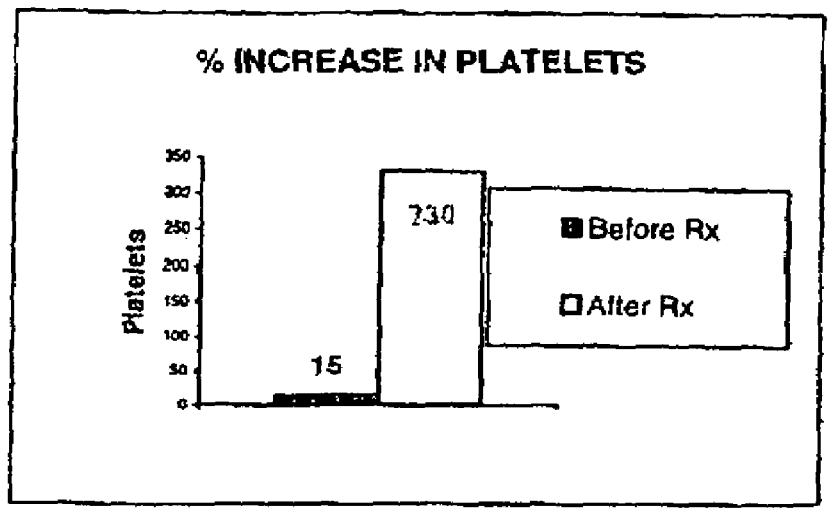
FIG. 4 illustrates the increase in platelet count caused by administering TISF to 23 cats infected with either FIV or FeLV. It shows a 200% increase in platelet count on average.
Figure 5:
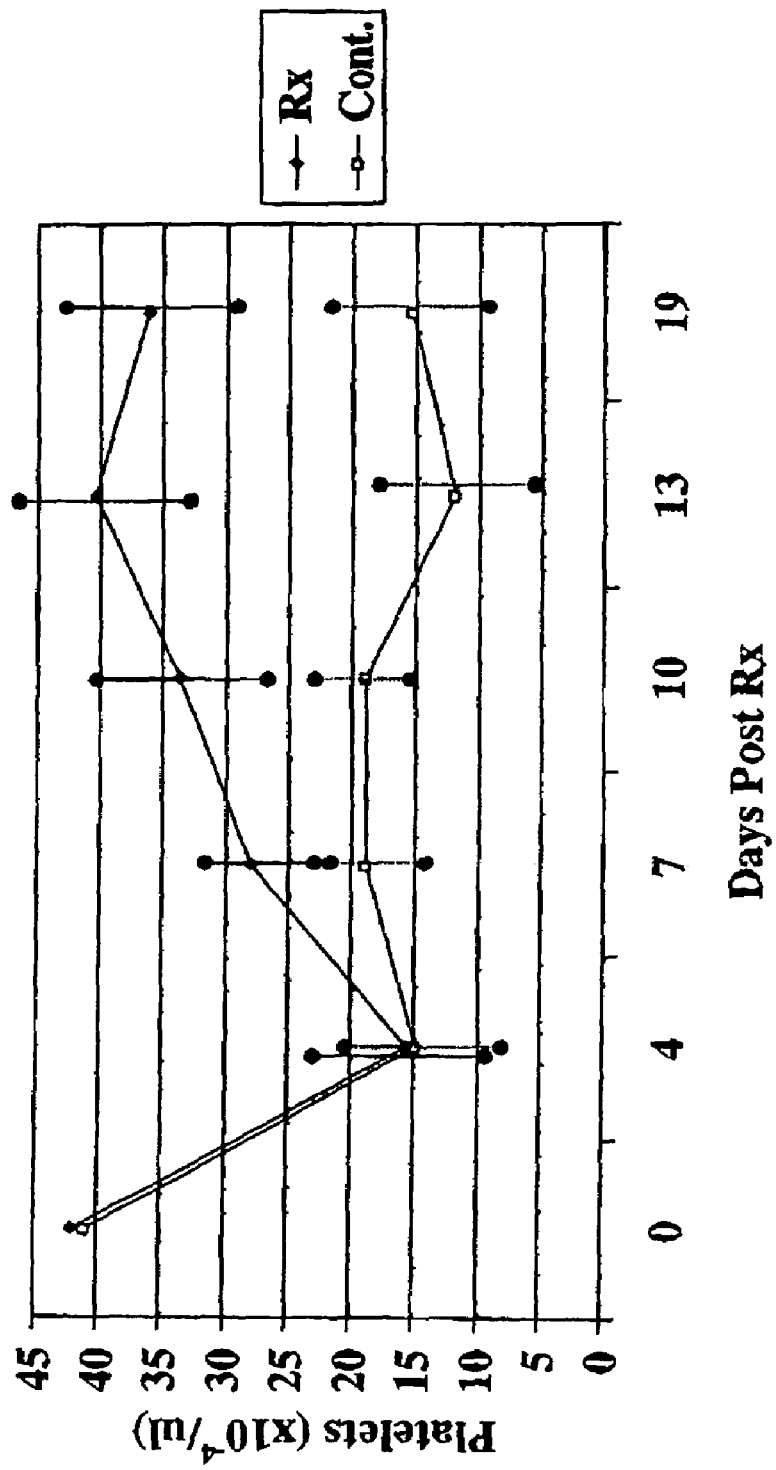
FIG. 5 is a graph of platelet count drop and recovery for mice in which platelet deficiency was induced by a chemotherapeutic treatment as described in T. R. Ulrich, et al., Blood 86, 971–71 (1995). It demonstrates that mice receiving TISF (referred to as S-Celergin) along with chemotherapy recovered to pre-treatment platelet count levels within about two weeks, while mice not receiving TISF showed little recovery in platelet levels after 19 days.

The cats initially diagnosed as deficient in one or more types of blood cell which were treated with TISF showed a statistically significant improvement on average, and the percentage of improvement was greatest in those animals where the deficiency was severe. See FIGS. 1–4.

EXAMPLE II

Using the procedures outlined in T. R. Ulrich, et al., Blood 86, 971–76 (1995), mice were treated with a chemotherapy agent alone or with the agent plus TISF. Platelet levels were then determined for each subject every few days post treatment. Four days after treatment, all animals showed a substantial drop in platelet levels, to less than half of the pre-treatment level on average. Subsequently, the subjects which did not receive TISF showed little change from days 4 to 19. The subjects treated with TISF showed statistically significant improvement in platelet levels by day 7, and by day 13 their platelets had returned to pre-treatment levels.

The foregoing detailed description of the invention and preferred embodiments, especially with respect to product compositions and processes, is to be considered illustrative of specific embodiments only. It is to be understood, however, that additional embodiments may be perceived by those skilled in the art. The embodiments described herein, together with those additional embodiments, are considered to be well within the scope of the present invention.

What is claimed as new and desired to be protected by Letters Patent of the United States is:

1. A method to stimulate the production of red blood cells in a subject, wherein said subject has been diagnosed as having a less than desirable level of red blood cells, which method comprises administering to said subject an amount of T-4 immune stimulating factor ("TISF") effective to elevate the red blood cell count.

2. The method of claim 1 wherein said less than desirable level of red blood cells is attributable to anemia.

3. A method to stimulate the production of granulocytes in a subject, wherein said subject has been diagnosed as having a less than desirable level of granulocytes, which method comprises administering to said subject an amount of TISF effective to elevate the granulocyte count.

4. A method to stimulate the production of platelets in a subject, wherein said subject has been diagnosed as having a less than desirable level of platelets, which method comprises administering to said subject an amount of TISF effective to elevate the platelet count.

5. A therapeutic protocol that comprises diagnosing a subject as having a less than desirable level of red blood cells, followed by administering to said subject an amount of TISF effective to elevate red blood cell count in said subject.

6. A therapeutic protocol that comprises diagnosing a subject as having a less than desirable level of granulocytes, followed by administering to said subject an amount of TISF effective to elevate granulocyte count in said subject.

7. A therapeutic protocol that comprises diagnosing a subject as having a less than desirable level of platelets, followed by administering to said subject an amount of TISF effective to elevate platelet count in said subject.

* * * * *